United States Patent [19]

Silverberg

[11] Patent Number: 4,755,184
[45] Date of Patent: Jul. 5, 1988

[54] BONE AUGMENTATION IMPLANT

[76] Inventor: Mark Silverberg, 2901 S. King Dr., Apt. #909, Chicago, Ill. 60616

[21] Appl. No.: 817,444

[22] Filed: Jan. 9, 1986

[51] Int. Cl.⁴ ............................................. A61F 2/28
[52] U.S. Cl. ...................................... 623/16; 623/66; 433/201.1
[58] Field of Search .................... 623/16, 66; 433/173, 433/176, 201.1; 128/92 YO

[56] References Cited

U.S. PATENT DOCUMENTS

| | | | |
|---|---|---|---|
| 3,739,773 | 6/1973 | Schmitt et al. | 128/92 YO |
| 4,430,760 | 2/1984 | Smestad | 128/92 YO X |
| 4,457,028 | 7/1984 | Draenert | 623/18 |
| 4,497,075 | 2/1985 | Niwa et al. | 623/16 |
| 4,657,548 | 4/1987 | Nichols | 623/10 |

OTHER PUBLICATIONS

Oral Surg. Aug., 1985, pp. 146-153.
J. Oral Maxillofac Surg. 43: pp. 3-7, 57-60; 277-280, 469-470, 570-573; 1985.
J. Oral Maxillofac Surg. 42: pp.89-92, 150-160, 224-230, 749-750; 1984.
J. Oral Maxillofac Surg. 41: pp. 629-642, 729-737, 801-706; 1983.

Primary Examiner—Richard J. Apley
Assistant Examiner—Alan W. Cannon
Attorney, Agent, or Firm—Collard, Roe & Galgano

[57] ABSTRACT

An implant for use in bone augmentation includes a hollow casing made of a resorbable material and a prosthetic filling material for bones contained within the casing. A method for bone augmentation includes the steps of making an incision adjacent to the augmentation site, inserting an implant comprising a hollow casing made of resorbable porous material and filled with a prosthetic filling material for bones, into the augmentation site directed via the incision, and closing the incision.

3 Claims, 9 Drawing Sheets

BONE AUGMENTATION IMPLANT

BACKGROUND OF THE INVENTION

This invention relates to an article and method for its use in bone augmentation. More particularly, it relates to an implant and a method for installing the implant, especially for rebuilding the underlying bones of the upper and lower jaw of one's mouth.

In humans, bone restoration or augmentation is often required after loss of teeth. Although a significant segment of the American population wears dentures, many of these people suffer from improper retention because of a resorption of the underlying alveolar bone. Many procedures have been proposed and applied to restore alveolar bone in order to improve denture retention and stability. (See J Oral Maxillofac Surg: 41:629–642, 729,737, 801–806, 1983; 42:89–92, 150–160, 224–230, 749–750, 1984; 43:3–7, 57–60, 277–280, 469–470, 570–573, 1985; and Oral Surg. Aug. 1985 p. 146.) For various reasons, the majority of these procedures are not totally satisfactory, and new materials and methods are constantly being developed.

Recently, a new class of hydroxylapatite has been developed which is thought to be the most biocompatible hard tissue found to date (see U.S. Pat. No. 4,097,935). Hydroxylapatite (HA) is a common mineral which is mined in large quantities as the principal source of phosphate ion for a variety of common products such as fertilizers and detergents. It is also used as a tableting and anti-caking agent, and as a calcium food supplement. As vertebrate tooth and bone mineral is derived from this chemical composition, it has long been the subject of medical investigation. HA makes up the bulk of the entire skeletal system, ranging from approximately 65% of bone to 98% of dental enamel and it would seem that HA is well tolerated when implanted into bone.

The most remarkable property of this material is its reputed ability to become directly bonded to bone by what appears to be a natural bone-cementing mechanism. In addition, HA is nonresorbable, i.e., it does not break down and assimilate into the body. Because of this attractive profile, particulate hydroxylapatite (HA) is being used to preserve alveolar bones which support the teeth, augment atrophic alveolar ridges, i.e., tooth socket bones which have shrunk due to lack of function, and to fill periodontal defects. Presently, prosthetic filling materials for bones, such as HA, are delivered into the augmentation site by injecting the loose material particles via a small bore insertion syringe. However, technical problems encountered with the current delivery system include displacement of particles into unintended locations and defects in the augmentation, with extrusion and loss of particles.

Accordingly, it is an object of the present invention to provide an article and method for improved restoration of defective living bones.

It is a more particular object of the present invention to provide such an article and method especially designed for improved preservation and augmentation of atrophic alveolar ridges.

It is also an object of the present invention to provide such an implant for restoration and augmentation of bones which is simple in design, easy and inexpensive to manufacture and use, effective, reliable and safe.

SUMMARY OF THE INVENTION

Certain of the foregoing and related objects are readily obtained with an implant for use in bone augmentation which includes a hollow casing made of a resorbable material and particles of a prosthetic filling material for bone contained within the casing. Preferably, the casing has pores and fits tightly around the particles so that some of the particles protrude through the pores. Most desirably, the casing is a mesh material, e.g., polyglycolic acid polymer, and the prosthetic filling material is hydroxylapatite. In a preferred embodiment, the implant is tubular with closed ends, and of variable lengths and diameter, as clinically required.

Certain of the foregoing and related objects are also attained in a method for bone augmentation which includes the steps of making an incision adjacent to the augmentation site, inserting an implant as described above into the augmentation site, preferably via a syringe, directed through the incision, and closing the incision. In a preferred embodiment, the augmentation site is an atrophic alveolar ridge. Preferably, the method additionally includes the step of maneuvering the implant by manipulating the overlying mucosa after the implant has been inserted. In addition, a plurality of implants may be inserted. Moreover, the implants may be wetted prior to implantation. The incision is preferably a single midline vertical incision extending from the ridge crest to the vestibule, or a bilateral vertical incision in the cuspid area. Most desirably, the incision is closed with mattress sutures.

Other objects and features of the present invention will become apparent in the following detailed description when taken in connection with the accompanying drawings which disclose one embodiment of the invention. It is to be understood that the drawings are designed for the purpose of illustration only and are not intended as a definition of the limits of the invention.

BRIEF DESCRIPTION OF THE DRAWINGS

In the drawings, wherein similar reference characters denote similar elements throughout the several views.

DETAILED DESCRIPTION OF THE PREFERRED EMBODIMENT

Figure 1:
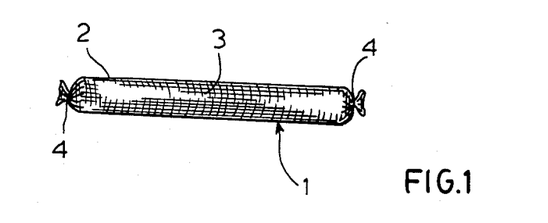
FIG. 1 is a front perspective view of a novel implant embodying the present invention.

Turning now in detail to the drawings and, in particular, to FIG. 1, therein illustrated is a novel implant embodying the present invention for use in bone reconstruction and, in particular, for augmentation of atrophic alveolar ridges. The implant 1 is composed of resorbable casing 2. Preferably, casing 2 is made of conventionally available polyglycolic acid (PGA) mesh, a high-molecular-weight linear polymer made by the ring opening polymerization of the purified glycolide monomer, although other suitable materials might be used e.g. polyglactin 910, i.e. polyglycolide co-galactide, available as Vicryl from Ethicon Co., New Jersey. In addition, bovine collagen or PDS (another absorbable suture material) or cellulose might possibly also be used as a casing material. The casing should be porous to allow tissue ingrowth to occur, and it should be resorbable to prevent a chronic foreign body reaction. The use of a permeable, biocompatable, absorbable tube fabricated from polyglycolic acid (PGA) mesh (Dexon) to contain the HA particles for implantation has been studied. Progressive absorption of the mesh along with the simultaneous ingrowth of connective tissue serves to maintain a desired contour during healing. PGA is available from American Cyanamid Company, Pearl River, N.Y.

Prosthetic bone filling material particles 3 are placed inside of casing 2 and it is then closed off at its ends 4. As described above, HA is the preferred prosthetic filling material for bone, although other materials, or newly developed materials may also be used. The openings of casing 2 are fine enough to prevent particles 3 from passing through it. If casing 2 is tightly wrapped around the particles 3, particles will protrude out through the pores in mesh. These protruding particles may promote earlier bone bonding as the presence of the mesh may have inhibited the formation of bone upon particles immediately adjacent to the cortical plate. The implant may be of varying length and diameter depending upon its intended use.

The mesh in various grades can also serve as a casing for cancellous bone, either alone, or mixed with prosthetic bone filling material. Also, by tightly wrapping the mesh around compressed cancellous bone, the use of cadaver bone to act as a crib while bone consolidation occurs, may be eliminated.

Figure 2:
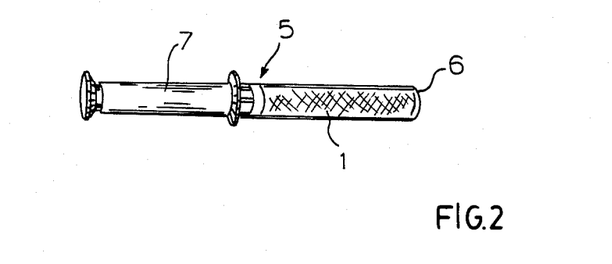
FIG. 2 is a front perspective view of an implant within a syringe which is used to assist in installing the implant.

Shown in FIG. 2 is an implant 1 within a small bore syringe 5 which in this case is used for inserting the implant under soft tissue of the patient's mouth. The implant to be inserted is slid into the open end of the syringe 6, with the plunger 7 drawn back. The implant is typically wetted with sterile saline solution prior to installation to facilitate lubrication and plasticity.

Figure 3:
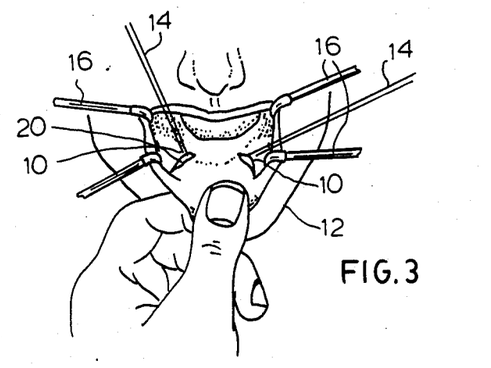
FIG. 3 is a front perspective view of a patient's mouth prepared for the augmentation procedure with incisions on either side of the lower jaw.
Figure 4:
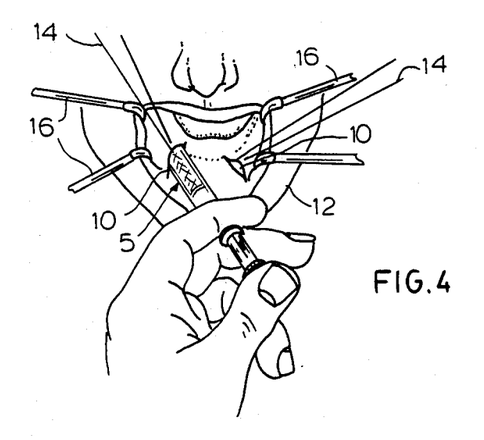
FIG. 4 is a front perspective view of a patient's mouth with a traction suture holding the incision open and the syringe ejecting the novel implant under soft tissue.
Figure 5:
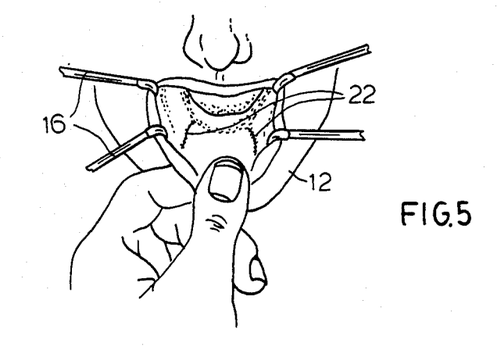
FIG. 5 is a front perspective view of the patient's mouth after the augmentation procedure with both incisions closed with interrupted sutures.

FIGS. 3, 4 and 5 show the instant method for installing the implant where the bone reconstruction involves augmentation of atrophic alveolar ridges of the jaw of one's mouth. FIG. 3 shows incisions 10 on either side of the lower jaw 12 held open with traction sutures 14. Retractors 16 adopted to provide a better view for photography, are disposed on both sides of the upper and lower lips. However, other types of retractors may also be used. The incisions are made in the soft tissue adjacent to the location where the augmentation is desired. The incisions are made large enough so that the body of the syringe can pass through and be manipulated into the proper position.

During the implant insertion, as shown in FIG. 4, the body of the syringe is passed through the incision opening, and the syringe is appropriately positioned. The plunger of the syringe is then depressed causing the implant to slide out the syringe and into the augmentation site. Sutures are used to hold the incision open so that the syringe may be more easily inserted and maneuvered. After the implant is inserted, the syringe is withdrawn. If necessary, the implant can be further maneuvered while in the augmentation site, by manipulating the overlying mucosa 20. The incisions are then closed, as shown in FIG. 5, via interrupted mattress sutures 22 or the like. For bone reconstruction in other areas of the body, the implant may be surgically installed.

The invention will now be explained in relation to several examples and experiments conducted by applicants which are given by way of example, and not of limitation.

EXAMPLES

Experiments were conducted to evaluate and compare morphologically, radiographically, and histologically the results of an implant containing a prosthetic filling material for bone as made according to the invention, and also of loose prosthetic material when placed in a surgically created subperiosteal pocket against a rat tibia. For the experiments, the implants of the invention were constructed out of PGA mesh tubes, and HA was used as the prosthetic material. The specific factors reviewed were soft tissue response, ability to bond to bone, displacement of particles, infiltration of surrounding tissue into the graft (bone vs. connective tissue), absorption of the mesh, and augmentation obtained. In addition, the length of time of resorption as well as local tissue reaction, measured by the amount of inflammatory response, were considered.

Materials and Methods

The implant casings were fabricated from sheets of PGA mesh supplied by the Davis and Geck Research Division of American Cyanamid Company, Pearl River, N.Y. A 12-gauge Angiocath catheter was used as a template upon which the casings were constructed, the casings therefore being formed into tubes. Subsequently, the catheter was used as a funnel to add the prosthetic material HA (2040), i.e., supplied by Calcitek Inc., San Diego, Calif. Each tube was approximately 2 mm in diameter by 5 mm in length. The implants were gas sterilized prior to the surgical procedure.

Twenty-seven white male Sprague-Dawley rats weighing between 400 and 450 gm were used for this study. The rats were anesthetized with ketamine, 0.2-0.4 mg, and xylazine, 0.1 mg, given intraperitoneally. After shaving and preparation of the surgical site, lidocaine, 2%, with 1:100,000 epinephrine, was infiltrated locally for vasoconstriction. An incision, 1.0 cm in length, was placed on the anteromedial surface of each hind leg over the broadest area of the tibial diaphysis. With retraction of the soft tissues, a small spoon excavator was used to elevate the periosteum and to create a subperiosteal pocket approximately 1.0-1.5 cm in length by 1.0 cm in width. The rats were divided into three groups according to the implant placed in the subperiosteal sleeve: (1) Group A: 3 rats, served as a control and underwent elevation of the periosteum and creation of a subperiosteal pocket but did not receive any implant. (2) Group B: 12 rats, receive bilateral implants of HA particles alone without mesh. This was accomplished with the use of an amalgam carrier. (3) Group C: 12 rats, received bilateral implants of previously fabricated PGA mesh tubes containing HA (PGA/HA). All incisions were closed with Dexon Plus suture (PGA suture coated with Poloxamer 188). The animals were then returned to individually marked cages. All animals had a stable postoperative course. There was no incidence of wound infection or wound dehiscence. One animal from Group A was sacrificed at 2 weeks, another at 6 weeks, and the third at 12 weeks. Three animals from Group B, and three from Group C were sacrificed at each of the following intervals: 2, 6, 12, and 18 weeks. Legs were disarticulated at the ileofemoral joint, after which the majority of the femur was sectioned off. Skin, and most of the muscle overlying the surgical site, was removed with scissors. Specimens were examined for attachment to underlying bone. Half of the specimens were then placed in 10% formalin in preparation for decalcification; the other half were placed in 70% ethanol in preparation for hard tissue sectioning and microradiographs.

The decalcified specimens were dehydrated, embedded in paraffin, cut to a thickness of 5 microns and stained with haematoxylin and eosin. The slides were examined for new bone formation, ingrowth of connective tissue, displacement of particles, and tissue response to the implant.

The undecalcified samples were dehydrated and defatted through a series of alcohol and ether-acetone washes, embedded in methyl methacrylate, and sectioned at 250 microns using an Adcock and Shipley milling machine. The samples were then ground to an average thickness of 175 microns for microradiographs and then further reduced to 160 microns for staining. According to Jowsey et al., the ideal thickness for microradiographs is 100 microns. Unfortunately, it was impossible to reach this thickness without loss of HA particles from the sections. Adequate microradiographs for morphology studies could, however, be obtained from 175-micron sections by directly placing the sections on high-resolution spectroscopic slides and exposing them to x-ray radiation at 25 KVP. The specimens were then ground to 160 microns and stained with paragon stain. The microradiographs and stained sections were then obtained and evaluated for bone growth, tissue healing, and absorption of PGA.

Results (A) Morphological Observations

After removal of the soft tissues, the implants were gently palpated to detect any mobility. Adherence to the recipient sites was observed at two weeks postimplantation but only when the graft was in close proximity to the cortical bone. Particles that had migrated away from the surface of the bone were movable with their surrounding soft tissues. This was observed more frequently when HA was implanted without PGA mesh. A less severe displacement was observed with a few of the PGA/HA implants involving the whole graft, with some proximity and resulting adherence always being maintained.

Figure 6:
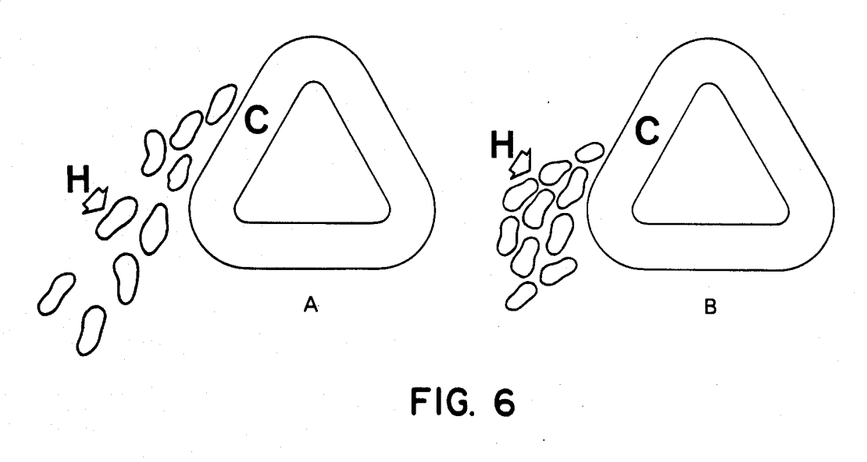
FIG. 6 is a schematic representation of a cross section of rat tibia demonstrating types of displacement observed.

FIG. 6(a) is a schematic representation of the prosthetic material, HA, implanted alone without mesh, while FIG. 6(b) shows the results of HA particles contained within a casing. The H designates the HA, and C designates the cortex. As can be seen, the HA material implanted without a PGA mesh casing became displaced from the implant site adjacent to the cortex. When contained within a PGA mesh casing, if displacement occurred it involved the whole implant with some contact with the cortical plate still evident.

(B) Measurement of Augmentation (Table 1)

Augmentation was assessed by measuring under the microscope the distance from the surface of the cortical plate to the outer surface of the implanted particles. Microradiographs (FIGS. 11-15) were obtained from two sections of each specimen for a total of six for each type of graft HA vs. PGA/HA for all time periods except HA at 2 weeks where only one specimen was available for preparation and observation. By using a scale etched onto one of the ocular lenses, measurements were made to the nearest 0.025 mm.

TABLE 1

| | HA | PGA/HA |
|---|---|---|
| 2 weeks | 1.1 mm | 1.6 mm |
| | | (range of 1.425-1.875) |
| 6 weeks | 1.0 mm | 1.4 mm |
| | (range of .75-1.375) | (range of 1.0-2.0) |
| 12 weeks | 1.0 mm | 1.5 mm |
| | (range of .70-1.324) | (range of 1.05-1.8) |
| 18 weeks | 1.0 mm | 1.3 mm |
| | (range of .75-1.225) | (range of 1.0-1.55) |
| | Composite average | |
| | 1.0 mm | 1.45 mm |

(C) Histological Observations

Decalcified sections of excised specimens were stained with haematoxylin and eosin and examined systematically.

Two Weeks

Group A: The sham operated control reveals well-defined areas of new woven bone sharply delineated from the lamellar bone of the cortex. This is noted at the periphery of the site of periosteal elevation. There is minimal inflammatory response composed of rare foreign body giant cells associated with suture material and a few histiocytes. In addition there is significant subperiosteal proliferation of young fibrous tissue with a suggestion of focal osseous metaplasia.

Group B: A similar picture is seen in rats that had HA implanted without PGA mesh. Sections show a periosteal aggregate of geometric spaces representing the HA particles. Each particle is encased by a thin layer of young fibrous tissue. As seen with the periosteal reaction, there is subperiosteal new bone formation and fibrosis adjacent to the cortical bone. Focal areas of osseous metaplasia of the fibrous tissue opposing the particles are noted. There is minimal inflammatory response with histiocytes and rare foreign body giant cells.

Group C: Rats that received the PGA/HA implants show the particles in place in a subperiosteal location, surrounded by the mesh and encased in granulation tissue with vascular and fibroblastic proliferation. Numerous foreign body giant cells, macrophages, and a few lymphocytes are noted. Again, reactive subperiosteal bone formation is present on either side of the implant particles. No osseous metaplasia is seen.

Six Weeks

Group A: The specimens show a slight increase in amount, and conversion of part of the woven bone to lamellar bone with focal areas of marrow formation. Again noted is the subperiosteal fibrosis which has increased in density containing areas of osseous metaplasia. An inflammatory or foreign body reaction is not present.

Group B: The subperiosteal woven bone is being replaced by lamellar bone. The particles, though close to the cortical bone, are separated from it by a thin layer of fibrous tissue There is some displacement of the particles into the adjacent muscle. No bone formation was noted between or around the particles. Few lymphocytes, histiocytes, and foreign body giant cells are seen in the fibrous tissue.

Figure 7:
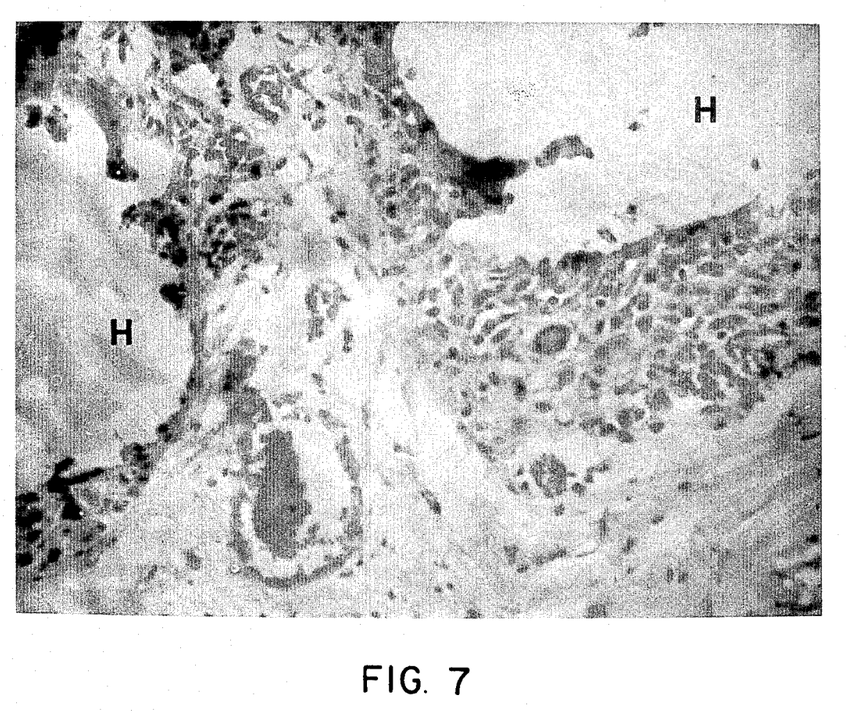
FIG. 7 is a microphotograph (Magnification ×100) of a decalcified rat tibia specimen with an implant according to the invention, six weeks after implantation.

Group C: The aggregate of particles is confined to the original implantation site by the mesh. The implants, as well as the individual particles, are surrounded by varying amounts of organizing granulation tissue with a foreign body reaction as shown in FIG. 7. Most of the woven bone is converted to lamellar bone. No significant osseous metaplasia is noted.

Twelve Weeks

Group A: The specimen shows all reactive bone converted to mature lamellar bone, and separated from the muscle by a thin fibrous layer. No further fibroblastic proliferation or osseous metaplasia is present. There is no significant increase in the thickness of the cortical plate.

Figure 8:
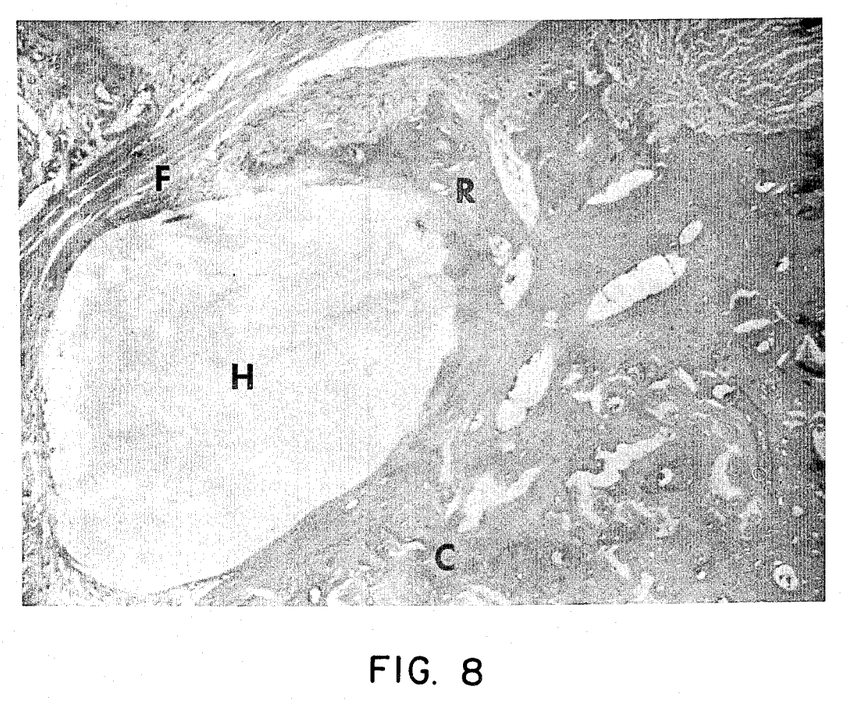
FIG. 8 is a microphotograph (Magnification ×40) of a decalcified rat tibia specimen, 12 weeks after implantation of prosthetic material particles without a casing.

Group B: Prominent features include severe displacement of the particles from the original implantation site some distance between adjacent muscle bundles, and converion of the reactive subperiosteal bone to lamellar bone. This is focally a close approximation of the particles to the adjacent new lamellar bone with some bone formation upon the surface of the particles. The connective tissue ingrowth and bone formation upon adjacent particles is shown in FIG. 8, wherein H designates HA, and F indicates interparticle fibrous stroma. The majority of the particles are surrounded by mature fibrous tissue. Occasional giant cells and macrophages were present.

Figure 9:
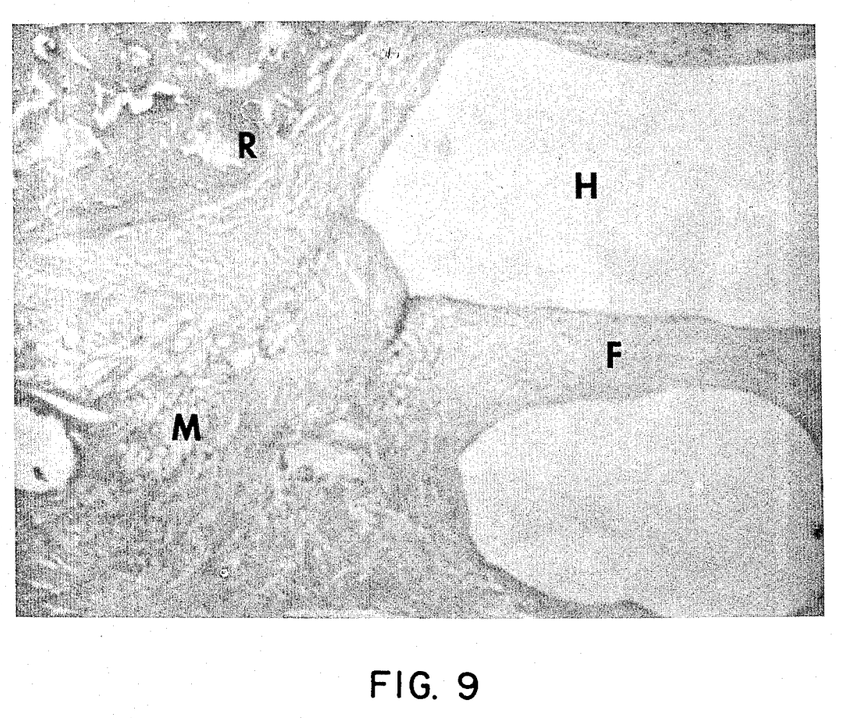
FIG. 9 is a microphotograph (Magnification ×40) of a decalcified rat tibia specimen with an implant according to the invention, 12 weeks after implantation.
Figure 10:
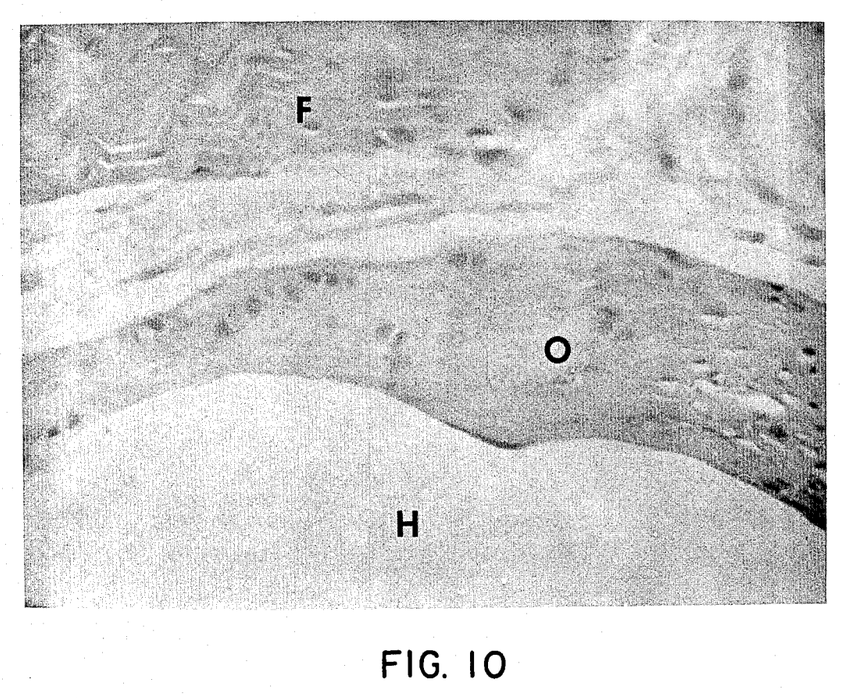
FIG. 10 is a microphotograph (Magnification ×100) of a decalcified rat tibia specimen with an implant according to the invention, 12 weeks after implantation.

Group C: The twelve week group C specimens shown in FIG. 9 had almost total resorption of the mesh with bonding and confinement of the particles by dense fibrous tissue which also separates the particles from the bone. FIG. 9 also shows the ingrowth of connective tissue, minimal foreign body reaction, and remnants of the mesh, indicated by M. FIG. 10 shows one specimen having osseous metaplasia with plump osteoblast-like cells focally adjacent to some of the particles. O designates osteoid metaplasia. There is a reduction in the foreign body reaction. Interestingly. one animal had a moderate lymphocytic reaction.

Eighteen weeks

Group B: No significant histological features are noted. All new bone is mature lamellar bone with all particles surrounded by dense connective tissue without evidence of osseous metaplasia or direct bonding to bone. No inflammation is present.

Group C: There is a disappearance of the mesh with minimal foreign body reaction. Fibrous tissue varying in density from loose to dense hyalinized tissue is present between the particles, and also bonding the particle aggregate to the bone. No particle displacement is seen and no bone was present between the particles.

(D) Studies on Undecalcified Specimens

Besides being used to measure augmentation, microradiographs were examined for displacement of particles and new bone formation.

Two Weeks

Figure 11:
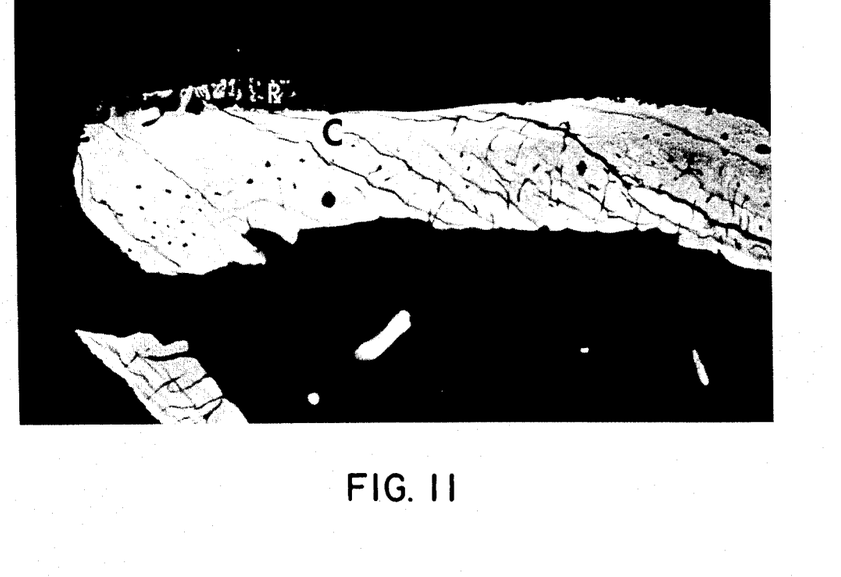
FIG. 11 is a microradiograph (Magnification ×10) of an undecalcified rat tibia specimen two weeks after elevation of the periosteum.

Group A: formation of subperiosteal (reactive) woven bone along the cortical surface in response to elevation of the periosteum, as shown in FIG. 11 is observed, as it was in the decalcified specimens (C designates cortex and R designates reactive bone).

Group B: HA particles in close proximity to the bone without displacement. A small amount of woven bone, as seen in group A, is evident.

Group C: Again, the reactive bone formation as seen in group A is observed. The particles are grouped together. In two specimens the graft is located at the edge of the cortical plate.

Six Weeks

Group A: A remodeling of the immature reactive bone to mature lamellar bone is observed.

Figure 12:
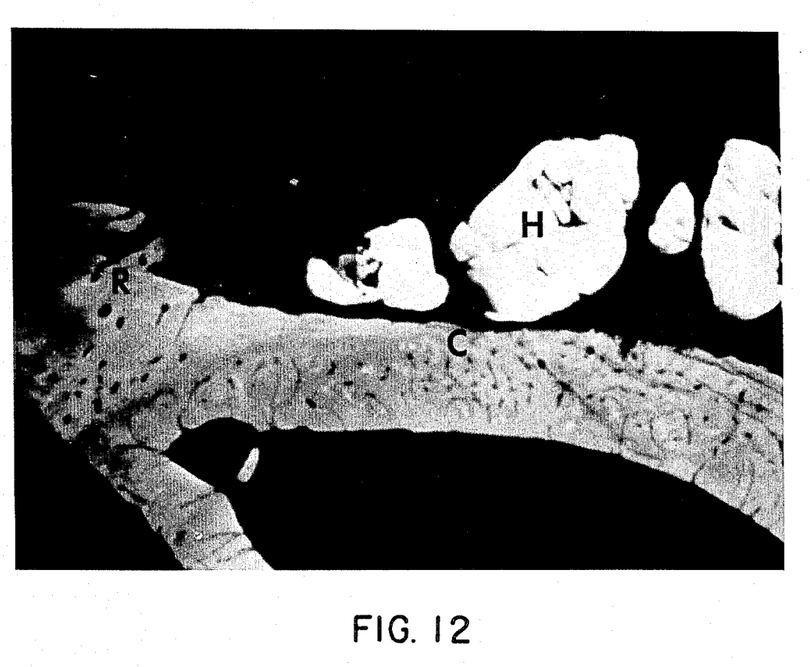
FIG. 12 is a microradiograph (Magnification ×10) of an undecalcified rat tibia specimen six weeks after implantation of prosthetic material particles without a casing.

Group B: FIG. 12 illustrates the displacement of particles with no direct bonding to bone and maturation of reactive bone to lamellar bone. The same bony reaction as seen in the decalcified specimen is observed.

Figure 13:
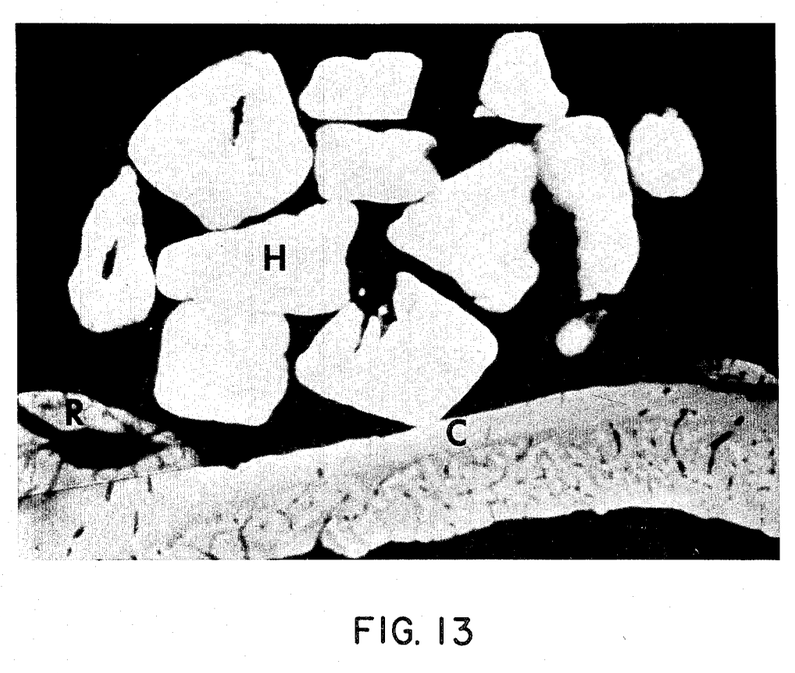
FIG. 13 is a microradiograph (Magnification ×10) of an undecalcified rat tibia specimen with an implant according to the invention, six weeks after implantation.

Group C: Particles are well contained adjacent to the cortical plate as shown in FIG. 13. The reactive bone has matured to lamellar bone with occasional marrow spaces, but still some woven bone is evident. No direct bonding of particles to bone is observed.

Twelve Weeks

Group A: A slight increase in the thickness of the cortical plate is observed.

Group B: Two of the specimens show the particles to be in good position adjacent to the cortical plate while in one specimen displacement of particles is noted. A few of the particles appear to be surrounded by reactive bone although a fine radiolucency intervenes. An irregular contour of the bony cortex is present adjacent to the particles.

Group C: The particles are grouped together and in two specimens appear to be located within a slight concavity of the cortex. In one specimen the graft is located at the edge of the cortical plate. The reactive bone is all lamellar bone.

Eighteen Weeks

Figure 14:
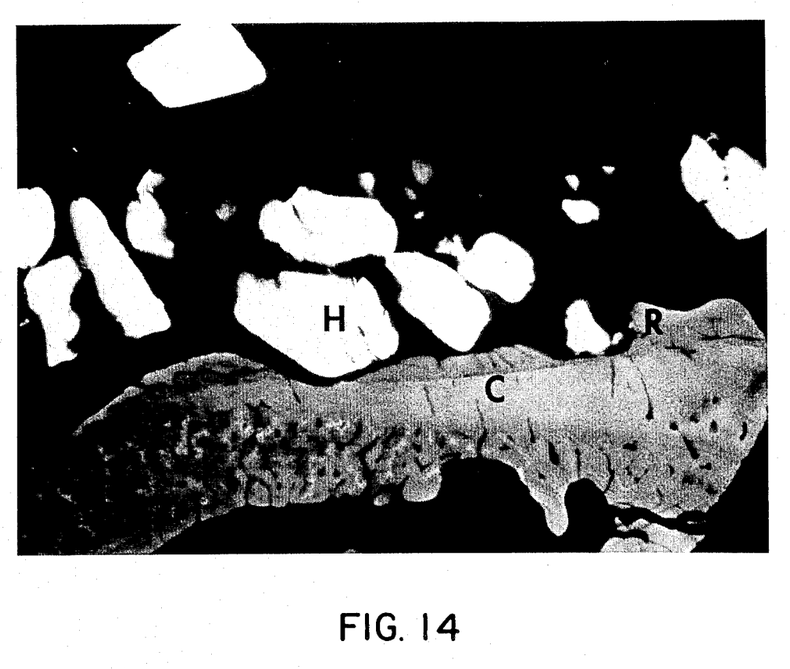
FIG. 14 is a microradiograph (Magnification ×10) of an undecalcified rat tibia specimen 18 weeks after implantation of prosthetic material particles without a casing.

Group B: As shown in FIG. 14, the displacement of the particles and irregularity of the cortical surface is essentially the same as that observed at twelve weeks.

Figure 15:
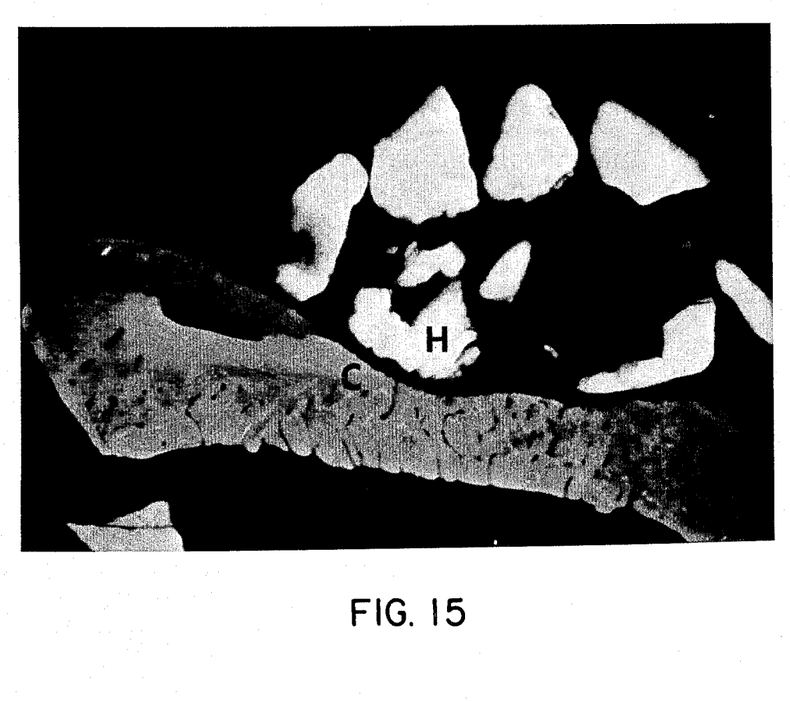
FIG. 15 is a microradiograph (Magnification ×10) of an undecalcified rat tibia specimen with an implant according to the invention, 18 weeks after implantation.

Group C: FIG. 15 shows the particles are neatly contained adjacent to the cortical plate. Again the implants appear to be positioned in a slight concavity of the cortical plate. There is no direct bonding to bone or growth of bone up through the particles.

Figure 16A:
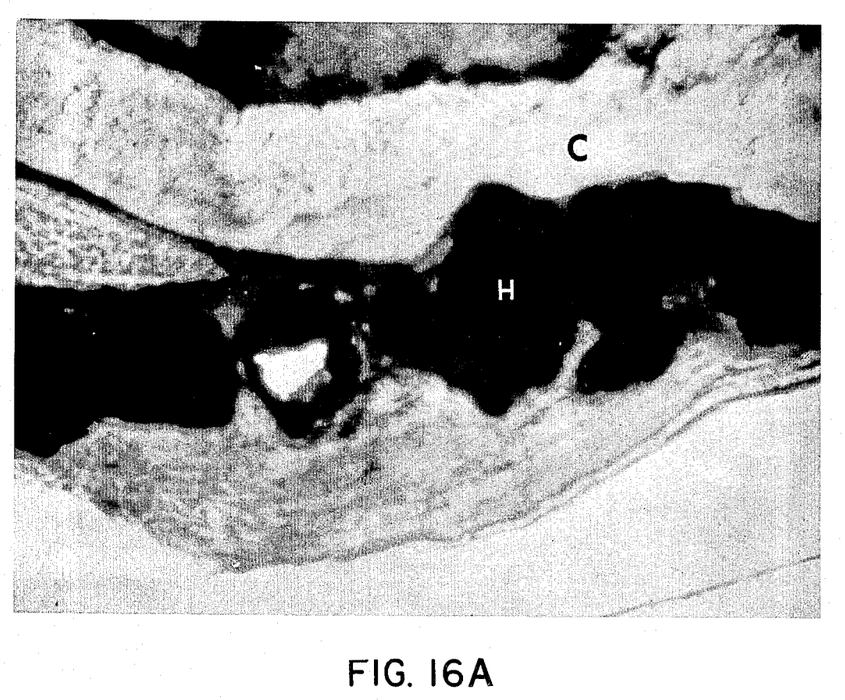
FIG. 16A is a microphotograph (Magnification ×10) of an undecalcified rat tibia specimen 18 weeks after implantation of prosthetic material particles without a casing.
Figure 16B:
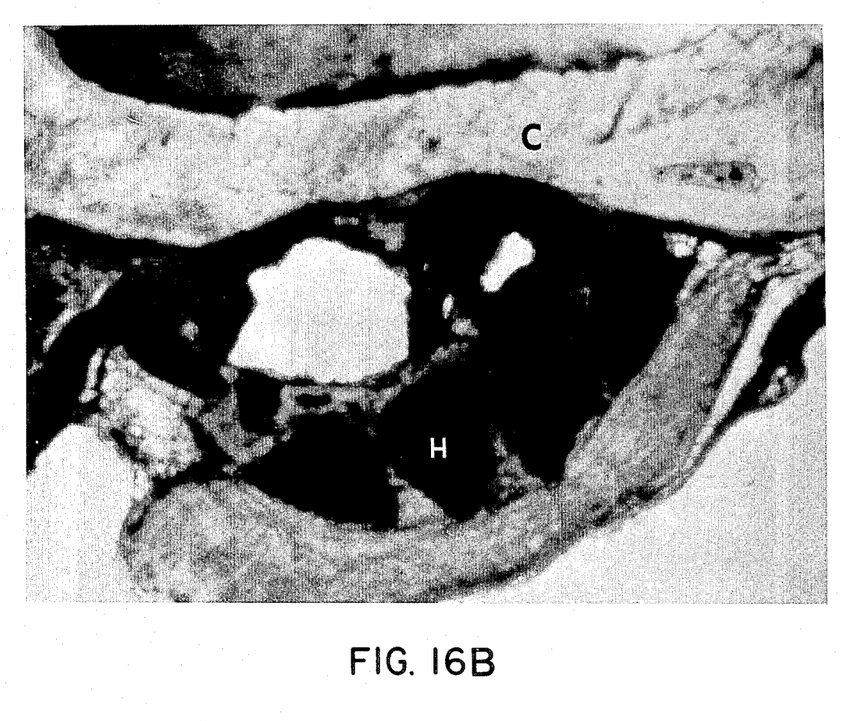
FIG. 16B is a microphotograph (Magnification ×10) of an undecalcified rat tibia specimen with an implant according to the invention, 18 weeks after implantation.

A comparison of FIG. 16A (a microphotograph of an HA implant without mesh at 18 weeks) to FIG. 16B (a microphotograph of an HA implant using PGA mesh) shows the greater and more controlled augmentation achieved using PGA mesh.

Paragon stain was used on the previous specimens to assess connective tissue ingrowth. Group B demonstrated a connective tissue ingrowth between the particles, which was moderately dense at two weeks and then increased in density and maturity, becoming more fibrous and less cellular by 6, 12, and 18 weeks. In specimens demonstrating bone growth surrounding an occasional adjacent particle there was always a clear separation by fibrous tissue. A good number of specimens showed severe displacement of particles into surrounding soft tissue.

Group C specimens also demonstrate a connective tissue ingrowth between the particles and surrounding the grafts, although at 2 weeks this had the appearance of a granulation tissue containing a prominent foreign body reaction. The mesh was visible at 2 and 6 weeks. Throughout the experimental period the surrounding connective tissue increased in density and maturity with the concomitant reduction of the foreign body reaction as absorption of the mesh occurred.

Polarized light microscopy nicely demonstrated the mesh at 2 weeks. By 6 weeks, absorption of the mesh was occurring with a more diffuse pattern of refractile material in the surrounding connective tissue. The mesh was greater than 95% absorbed by 12 weeks and greater than 99% absorbed by 18 weeks.

CONCLUSION

The test results establish that the casing effectively contained the prosthetic material, preventing severe displacement of particles and therefore resulting in greater augmentation. It was also concluded that connective tissue ingrowth is not inhibited by PGA mesh and that after absorption of the casing, one is essentially left with the same histological picture as with prosthetic material without a casing.

The experiments also indicate that the new delivery system for prosthetic material effectively contained the particles for implantation and that the casing was progressively absorbed over a period of approximately 9 weeks. During this time, connective tissue ingrowth occurred, resulting in the gross stabilization of the particles and implant as a unit. As observed in this study a 45% greater augmentation was achieved using the implant. If this is applied to the clinical situation, using this novel implant to contain the prosthetic material may result in the use of less of the prosthetic material for a significantly greater augmentation.

The progressive absorption of the casing avoids the problems of a chronic foreign body reaction, which is proportional to the amount of material implanted. The implants used in the experiments because of their small size, had a proportionally large surface area and therefore a large PGA:HA ratio. If one uses a larger implant and stretches the casing to barely contain the particles, this ratio, and therefore the tissue response, can probably be significantly decreased.

The presence of the casing may have inhibited the formation of bone upon particles immediately adjacent to the cortical plate, although after absorption of the casing had progressed, there was evidence in one specimen of early bone or cartilage formation upon the surface of an interfacing particle. When the casing was tightly wrapped around the prosthetic material particles, it was noted that particles protruded out through pores in the mesh. By overfilling the casing prior to implantation, earlier bone bonding may be promoted.

The topic of bone bonding deserves further discussion. As demonstrated in the control group, simply elevating the periosteum results in the formation of reactive bone. Particles that were in the immediate area of reactive bone formation, although few in number, were partially surrounded by this bone. Contrary to what is in the literature, it seems unlikely that HA alone stimulates osteogenesis and more likely that elevation of the periosteum is the responsible factor.

There is also no mention in the literature of the possibility of the HA causing resorption of underlying bone. On cross-sectional histological examination this would give the same appearance as bone ingrowth and may be why Chang et al.[11] observed bone ingrowth through half of the graft (thickness not stated) by 9 months. The findings also suggest deposition of surrounding bone and/or resorption of underlying bone as demonstrated in the 12 and 18-week microradiographs. Future research to determine whether this is clinically relevant seems warranted. Results of this preliminary study seem promising. Since after absorption of the PGA mesh, one is left with essentially the same histological picture as HA implanted alone without mesh and a greater augmentation, it does seem that this technique would be useful in humans.

It should be apparant that other variations may be made as will be apparant to those skilled in the art. Thus while only one embodiment of the present invention has been shown and described, it will be obvious that many changes and modifications may be made thereunto, without departing from the spirit and scope of the invention.

What is claimed is:

1. An implant for use in alveolar above bone augmentation which provides a stress-bearing prosthesis, comprising:
    a hollow casing formed of a porous mesh, resorbable polyglycolic acid polymeric material; and
    hydroxylapatite prosthetic filling material particles contained within said casing, some of said particles protruding through said mesh casing wherein the porous mesh size is smaller than the mesh size of said particles to preclude escape of said particles.

2. The implant according to claim 1, wherein said mesh material is polyglycolide co-galactide.

3. The implant according to claim 1, said casing is tubular and has closed ends.

* * * * *